(12) United States Patent
Stencel

(10) Patent No.: US 7,770,455 B2
(45) Date of Patent: Aug. 10, 2010

(54) INSTRUMENTS, RELATED SYSTEMS, AND METHODS FOR MONITORING OR CONTROLLING FOAMING

(75) Inventor: John M. Stencel, Lexington, KY (US)

(73) Assignee: Tribo Flow Separations, LLC, Lexington, KY (US)

( * ) Notice: Subject to any disclaimer, the term of this patent is extended or adjusted under 35 U.S.C. 154(b) by 362 days.

(21) Appl. No.: 10/588,091

(22) PCT Filed: Mar. 16, 2005

(86) PCT No.: PCT/US2005/008817

§ 371 (c)(1),
(2), (4) Date: Jul. 28, 2006

(87) PCT Pub. No.: WO2005/098377

PCT Pub. Date: Oct. 20, 2005

(65) Prior Publication Data

US 2007/0131033 A1    Jun. 14, 2007

Related U.S. Application Data

(60) Provisional application No. 60/553,637, filed on Mar. 16, 2004.

(51) Int. Cl.
*G01N 29/00* (2006.01)
*G01N 24/00* (2006.01)
(52) U.S. Cl. .................. 73/589; 73/60.11; 73/64.41
(58) Field of Classification Search .................. 73/587, 73/584, 574, 589, 591, 579, 592, 60.11, 61.41, 73/64.41, 64.43
See application file for complete search history.

(56) References Cited

U.S. PATENT DOCUMENTS

| 3,246,516 | A |   | 4/1966  | Maropis            |
|-----------|---|---|---------|--------------------|
| 4,184,371 | A |   | 1/1980  | Brachet            |
| 4,325,255 | A |   | 4/1982  | Howard et al.      |
| 4,397,561 | A | * | 8/1983  | Strong et al. ............ 366/21 |
| 4,624,745 | A |   | 11/1986 | Sande et al.       |
| 4,640,130 | A |   | 2/1987  | Sheng et al.       |
| 4,934,177 | A |   | 6/1990  | Cuthbertson et al. |
| 5,108,655 | A |   | 4/1992  | Johns, Jr. et al.  |
| 5,469,854 | A | * | 11/1995 | Unger et al. ............ 600/458 |

(Continued)

FOREIGN PATENT DOCUMENTS

EP    0 697 583    2/1996

OTHER PUBLICATIONS

Boyd, Varley; "The uses of passive measurement of acoustic emissions from chemical engineering processes"; Chemical Engineering Science 56; 2001; pp. 1749-1767; Elsevier Science Ltd.; Department of Chemical Engineering and Chemical Technology, Imperial College of Science, Technology, and Medicine; London, England.

(Continued)

*Primary Examiner*—Helen C. Kwok
(74) *Attorney, Agent, or Firm*—King & Schickli, PLLC

(57) ABSTRACT

The present invention relates to methods, systems, and instruments (10) for monitoring, detecting or measuring one or more acoustic emissions of a foam. The detected emission(s) may then be used to generate a response, such as one to control an associated process.

9 Claims, 15 Drawing Sheets

U.S. PATENT DOCUMENTS

| | | | |
|---|---|---|---|
| 5,656,428 | A | 8/1997 | McAllister et al. |
| 5,775,803 | A * | 7/1998 | Montgomery et al. .......... 366/2 |
| 5,868,859 | A | 2/1999 | Hei et al. |
| 6,082,174 | A | 7/2000 | Lee et al. |
| 6,385,558 | B1 | 5/2002 | Schlemm |
| 6,397,665 | B1 | 6/2002 | Kirts et al. |
| 6,405,580 | B2 | 6/2002 | Kirts et al. |
| 6,461,414 | B1 | 10/2002 | Kohl et al. |
| 6,484,568 | B1 * | 11/2002 | Griffith et al. ............... 73/60.11 |
| 6,491,421 | B2 * | 12/2002 | Rondeau et al. ................ 366/8 |
| 6,507,790 | B1 | 1/2003 | Radomski |
| 6,542,828 | B2 | 4/2003 | MacDonald et al. |
| 6,590,000 | B2 | 7/2003 | Varadaraj |
| 6,640,618 | B2 | 11/2003 | Kirts et al. |
| 6,874,356 | B2 * | 4/2005 | Kornfeldt et al. .......... 73/64.42 |
| 6,964,302 | B2 * | 11/2005 | Luke et al. .................. 166/293 |
| 7,153,396 | B2 * | 12/2006 | Genser .......................... 203/1 |

OTHER PUBLICATIONS

Goddard, Forster; "Stable foams in activated sludge plants"; Enzyme Microb. Technol., 1987; pp. 164-168, vol. 9; Department of Civil Engineering, Birmingham University; Birmingham, England.

Dodson, Ph.D.; "Concrete Admixtures"; Structural Engineering Series; pp. 139-149; Van Nostrand Reinhold, New York.

Hossain, Wun Jern, Say Leong; "Control of Activated Sludge Foaming"; pp. 771-778; Dept. of Civil Engineering, National University of Singapore; Singapore.

Brown, Kaul, Varley; "Continuous Foaming for Protein Recovery: Part II. Selective Recovery of Proteins from Binary Mixtures"; Biotechnology and Bioengineering, Feb. 1999; pp. 291-300, vol. 62, No. 3; John Wiley & Sons, Inc.; Biotechnology and Biochemical Engineering Group, Food Science and Technology Dpt., The University of Reading; Reading, England.

Lockwood, Bummer, Jay; "Purification of Proteins Using Foam Fractionation"; Pharmaceutical Research, 1997; pp. 1511-1515, vol. 14, No. 11; Plenum Publishing Corporation.

Banhart, Stanzick; "Metal foam evolution studied by synchrotron radioscopy"; App. Phys. Letters, Feb. 2001; pp. 1152-1154, vol. 78, No. 8; American Institute of Physics; Germany.

Rzeszotarska, Rejmund, Ranachowski; "Acoustic emission measurement of foam evolution in H2O-C2H5OH—air systems with content of detergent triton X-100"; Ultrasonics, 1998; pp. 953-958; Elsevier Science B.V.; Institute of Fundamental Technological Research Problems; Warsaw, Poland.

Pollock; "Acoustic Emission Inspection"; Physical Acoustics Corporation, Technical Report, 2003; MISTRAS Holdings Group.

Wilson; "Cement and Concrete: Environmental Considerations"; Environmental Building News, Mar./Apr. 1993; vol. 2, No. 2; BuildingGreen, Inc.

"React"; Physical Acoustics Corporation, 2003; MISTRAS Holdings Group; Princeton Jct, New Jersey.

Weaire, Hutzler; "The Physics of Foams", 2003; Oxford Press, ISBN 0-19-851097-7.

Vandewalle, Lentz, Dorbolo, Brisbois; "Avalanches of Popping Bubbles in Collapsing Foams"; Phys. Rev. Lett., 2001; vol. 86.

Hill, Manross, Davidson, Palmer, Nutt, Ross; "Sensing and Control Systems: A Review of Municipal and Industrial Experiences"; WERF Report 99-WWF-4; 2002, IWA Publishing.

* cited by examiner

INSTRUMENTS, RELATED SYSTEMS, AND METHODS FOR MONITORING OR CONTROLLING FOAMING

This application claims the benefit of U.S. Provisional Patent Application Ser. No. 60/553,637, filed Mar. 16, 2004, the disclosure of which is incorporated herein by reference in its entirety.

TECHNICAL FIELD

The present invention relates generally to monitoring or controlling foaming and, more particularly, to instruments, related systems, and methods for use in characterizing, monitoring, or controlling any foaming process or object (gas, liquid, or solid) susceptible to foaming.

BACKGROUND OF THE INVENTION

Foams or emulsions (hereinafter collectively referred to as "foams") are ubiquitous in various processing operations. Foam sometimes creates or provides certain desirable product characteristics, such as a specific consistency of food or taste in a beverage (e.g., beer), and is thus considered advantageous. Other times, foam is an undesired byproduct, such as during wastewater treatment. In such cases, the foam must be eliminated, or at least monitored and kept in check.

Many systems and processes rely on human intervention for monitoring and controlling foaming. For instance, the concrete industry and associated cement, mineral admixture and chemical admixture supplier industries, use visual, subjective measurements or ASTM methods to determine both the level to which air entraining agents, or "AEA's," are to be dosed into concrete mix to meet construction specifications and to gauge stability and the foaming characteristics of AEA's. AEA use is mandated by state and U.S. federal transportation agencies in concrete highway and bridge construction and in building construction standards (e.g., ACI 318 Building Code) whenever temperatures below 32° F. are experienced.

To gauge the proper amount of AEA to be added to concrete mix, tests are manually performed beforehand on a sample to assess the foam stability. This testing involves a visual inspection of the sample to monitor the behavior of the foam, such as the amount of bubbles breaking in the foam over a given time period, to assess whether more AEA must be added (in which case the test is repeated until the appropriate amount is determined). Obviously, this is not only a time consuming, laborious process that can lead to frustration, but also a highly subjective one that often leads to an inconsistent end product.

Similarly, under current industry-wide practices, wastewater plants manually measure and monitor the level of foam created during the aeration portion of the treatment process. This requires workers to visually inspect, manually extract, and perform optical measurements on water samples to quantify the cause of the excessive foaming (which is typically microbial in nature) and take appropriate corrective measures. This is a laborious undertaking involving careful sampling and analysis of the resulting data. Moreover, reestablishing a proper balance of microbes or other operational parameters of the system can take up to one week. This time delay increases the probability of excessive foaming in the interim, which can ultimately lead to a deleterious and hazardous overflow requiring emergency measures to control or contain.

Accordingly, the need exists for an automated manner for monitoring or controlling foaming, whether created for beneficial purposes or otherwise. The approach taken should be capable of monitoring the foam with the ability to make an objective characterization. Appropriate control measures could then be taken based on this characterization, such as to increase, decrease, or stabilize the foaming. Together, this monitoring and control would decrease the amount of manual labor and subjectivity in characterizing the foam, thus providing a significant savings in terms of time and money in a myriad of commercial and industrial processes.

SUMMARY OF THE INVENTION

In accordance with one aspect of the invention, an instrument for intended use in monitoring or controlling a foam associated with a process or object is disclosed. The instrument comprises a passive sensor for generating an output signal representative of an acoustic emission associated with the foam and a controller in communication with the passive sensor for receiving the output signal and providing a response.

In one embodiment, the object is a liquid and the response comprises a signal for activating a source of foam suppressant positioned adjacent the liquid. The signal may also be for activating an alert selected from the group consisting of a signal for generating an audible alarm, a signal for dialing a telephone number, and a signal for displaying data on a display device. The instrument may further include a plurality of passive sensors positioned adjacent to the process or object.

In other embodiments, the instrument is used in combination with various systems. One such system is for testing a mixture for making concrete, and further comprises a vessel for receiving the mixture. The system may further include a source of an air entraining agent, in which case the response may comprise a signal for causing the source to add the agent to the mixture. An agitator may be associated with the vessel, and the response may comprise a signal for activating the agitator.

Another possible use is with a system including a column of liquid susceptible to foaming. In such a system, at least one input receives a flow of gas to create a foam on a surface of the liquid column. In such case, the passive sensor may be a hydrophone positioned at or below the surface of the liquid in the column. The instrument may further include a plurality of passive sensors, wherein a first of the sensors is positioned above the surface of the liquid and a second of the sensors is positioned at or below the surface of the liquid.

Yet another use of the instrument is in combination with a system for heating and curing of a foam formed from a precursor material including a heater for heating the precursor material. The response in such case may be to control the heater. Alternatively, the response may be to generate a signal to remove the precursor material from the heater.

In accordance with another aspect of the invention, a method of process monitoring and control is disclosed. The method comprises detecting an acoustic emission of a foam and actuating a response based on the detected acoustic emission. The detecting step may comprise placing a passive sensor in acoustic communication with the foam. Preferably, the actuating step is completed only once a threshold level of the acoustic emission is exceeded and further comprises sending an alert selected from the group consisting of generating an audible alarm, dialing a telephone number, or displaying data representative of the acoustic emissions on a display device. Alternatively, actuating may comprise taking steps to automatically control a level of the foam.

In accordance with still another aspect of the invention, a method of testing a mix used to form concrete is disclosed.

The method comprises adding an agent to the mix, detecting one or more acoustic emissions of the mix, and determining whether an additional amount of the agent is required. The agent may be an air entraining agent and the step of measuring may comprise receiving the acoustic emissions from a foam associated with the mix.

The adding and detecting steps may be completed using only a sample of the mix. In that case, the method may further include determining whether to add an additional amount of the agent based on the detected acoustic emissions. When an appropriate amount of the agent is added, the method may include creating a larger batch of the mix by adding an amount of the agent proportional to the amount added to the sample.

BRIEF DESCRIPTION OF THE DRAWING FIGURES

FIG. 1 schematically illustrates one possible embodiment of the instrument forming one aspect of the present invention;

Figure 2:
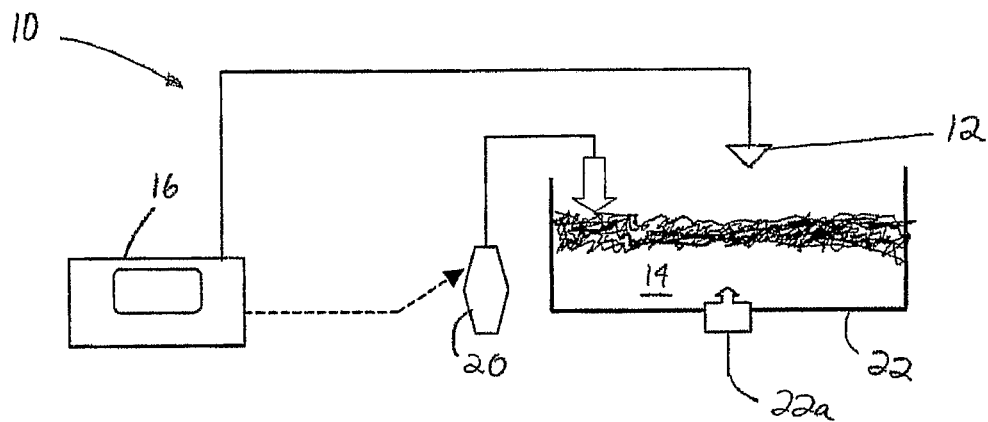
Figure 2A:
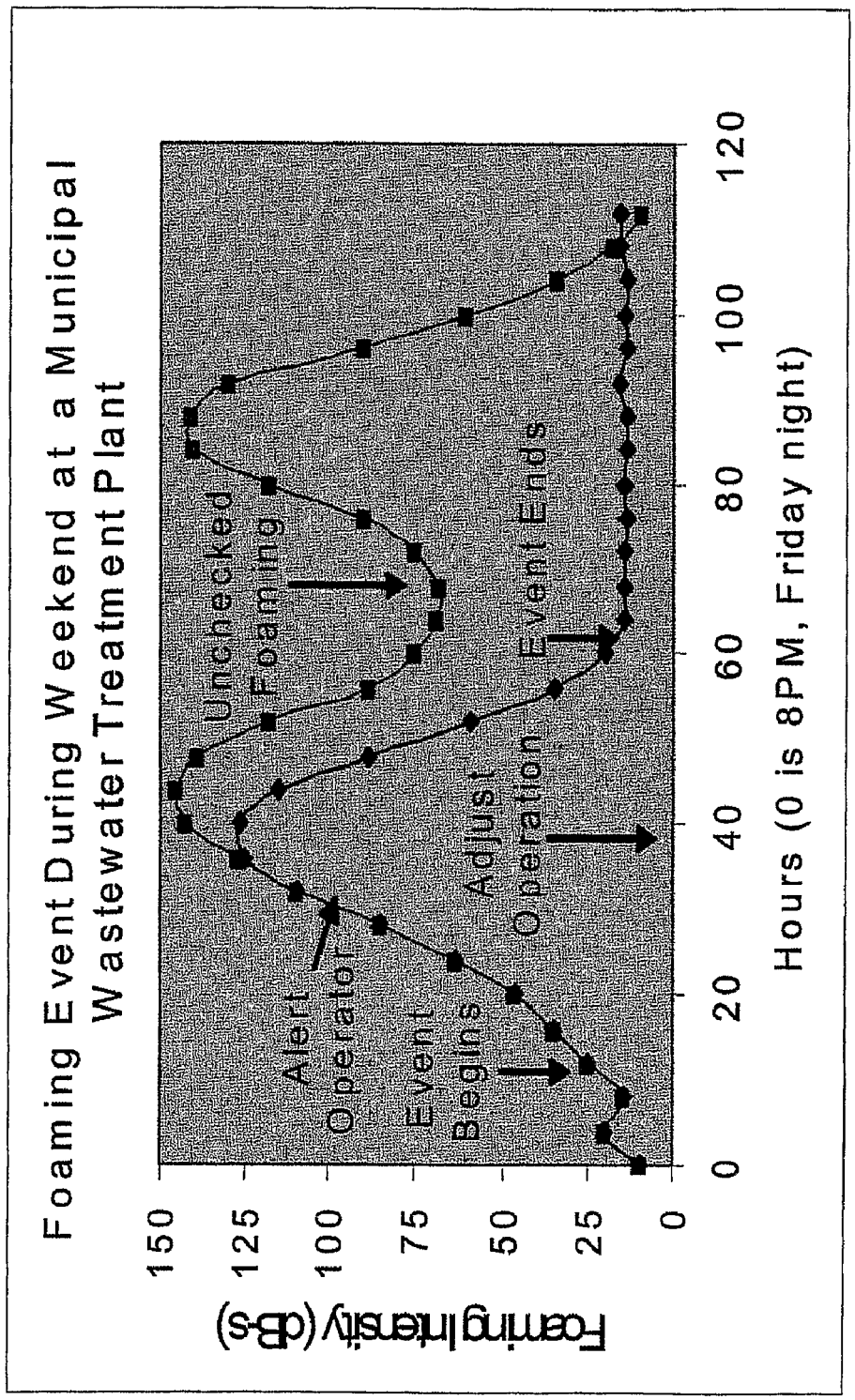
Figure 3:
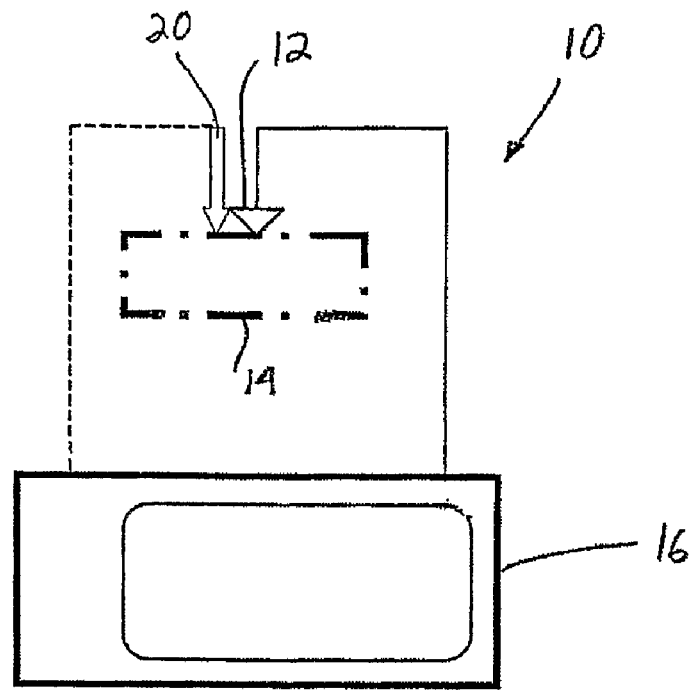
Figure 4A:
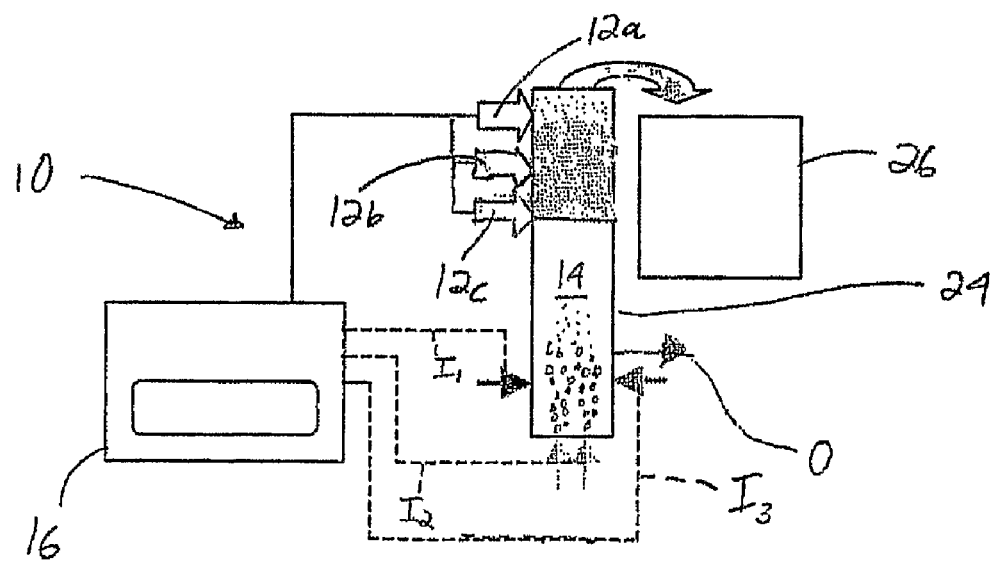
Figure 4B:
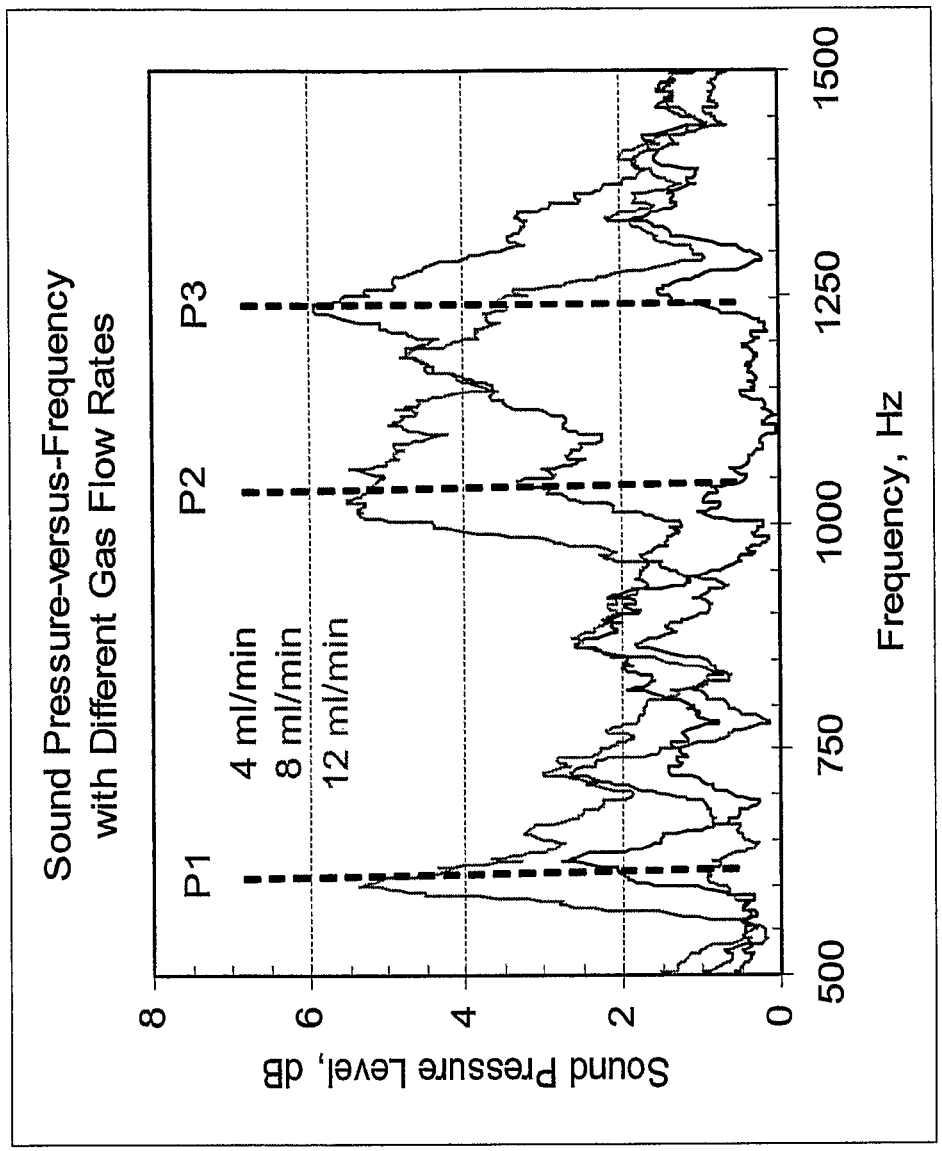
Figure 5:
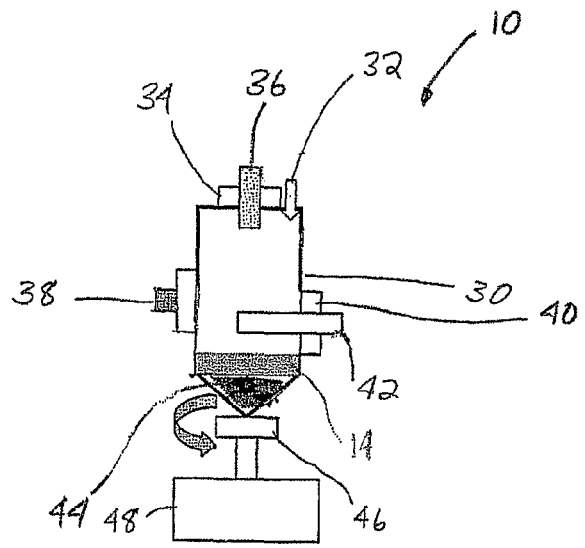
Figure 6:
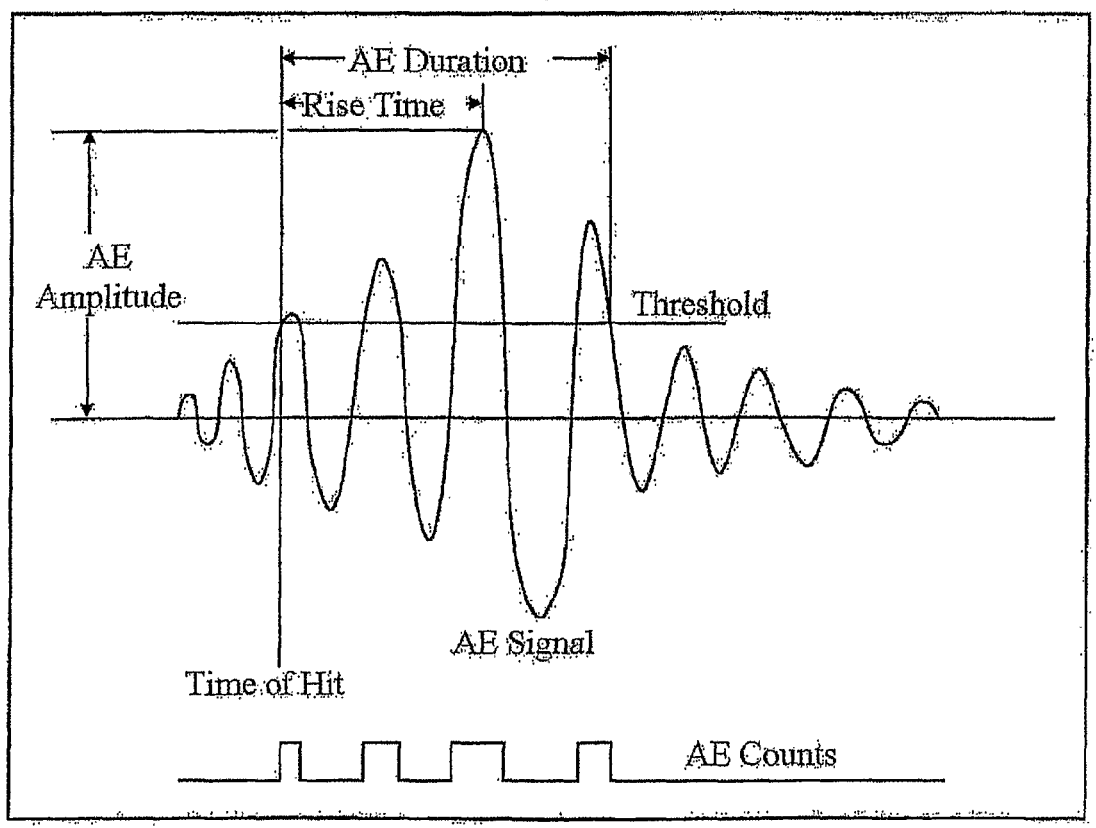
Figure 12:
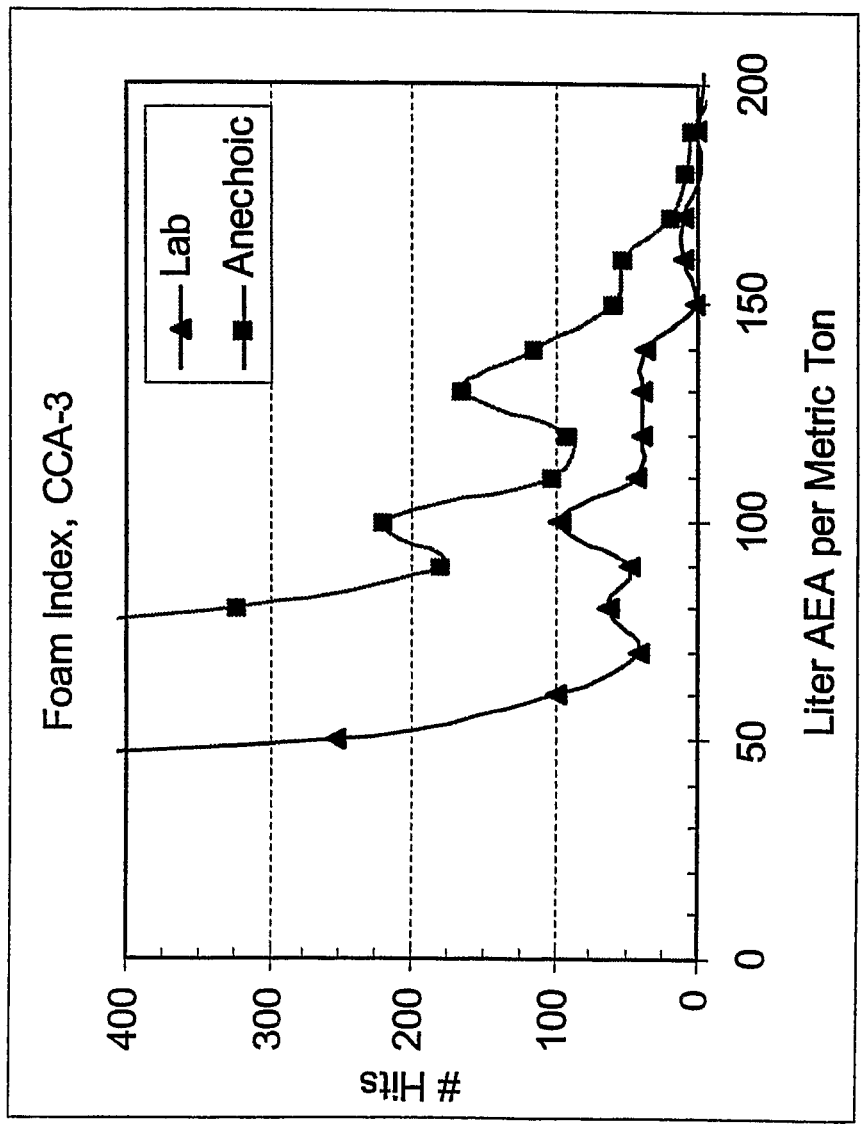
Figure 13:
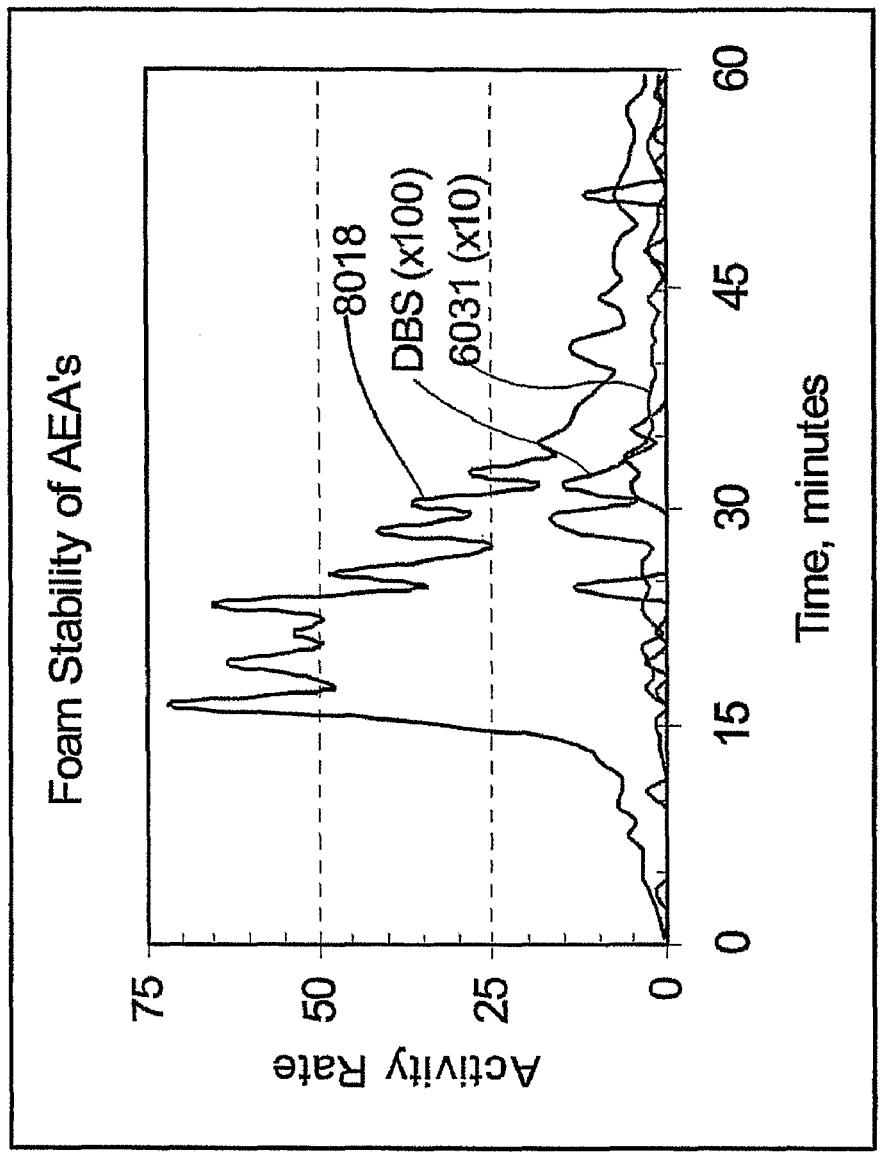
Figure 14:
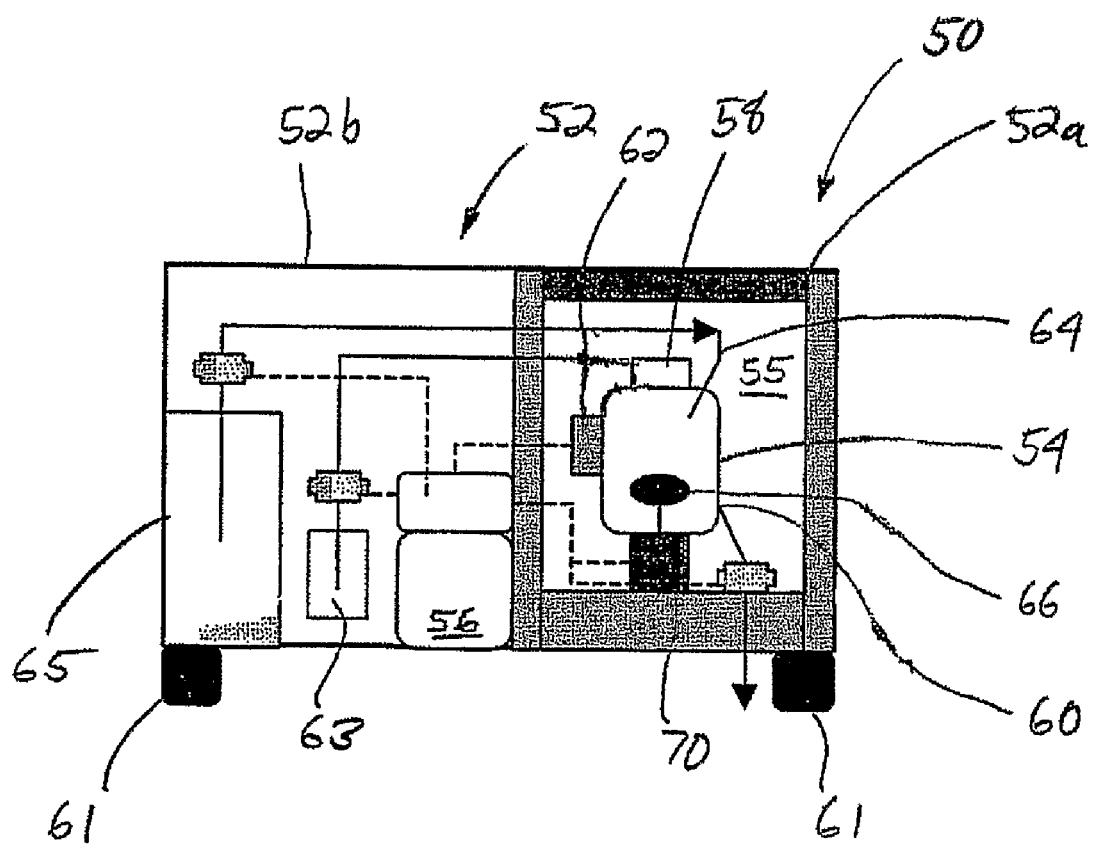

FIG. 2 schematically illustrates use of the instrument in a wastewater treatment system;

FIG. 2a graphically illustrates a hypothetical foaming event at a wastewater plant;

FIG. 3 schematically illustrates using acoustic emission techniques in materials processing;

FIG. 4a schematically illustrates using acoustic emission techniques in foam fractionation;

FIG. 4b illustrates the results of using acoustic emission techniques in foam fractionation;

FIG. 5 schematically illustrates another use of acoustic emission techniques;

FIG. 6 graphically illustrates acoustic emission waveform characteristics;

FIGS. 7-13 graphically illustrate the viability of using acoustic emissions to assess a foam index; and FIG. 14 schematically illustrates another embodiment of a foam index test instrument.

DETAILED DESCRIPTION OF THE INVENTION

Figure 1:
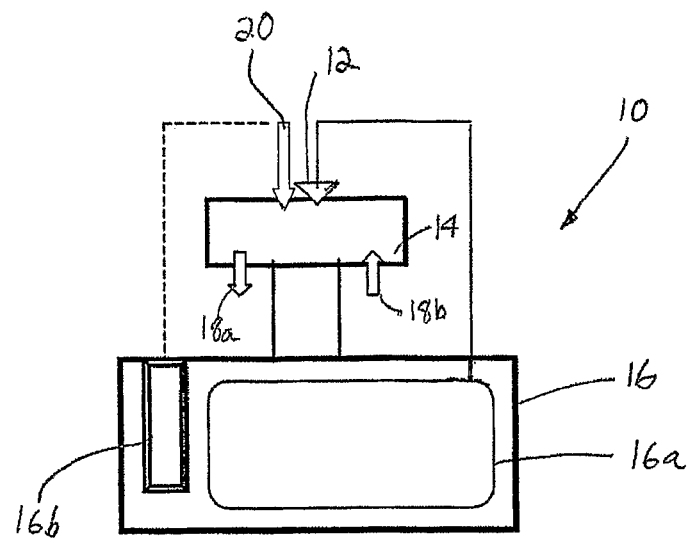
FIG. 1a shows acoustic emissions used to assess a foam index of Portland Cement.
FIG. 1b illustrates acoustic emission intensity versus AEA added to Portland Cement.

FIG. 1 schematically illustrates one possible embodiment of a test instrument 10 forming one aspect of the present invention. In its most basic form, the instrument 10 includes a sensor, such as a passive acoustic sensor 12, positioned in or adjacent to a given object, such as a container or vessel holding a substance 14 susceptible to foaming, and an associated controller 16. In one embodiment, the instrument 10 measures the acoustic emissions generated by an emulsion or a foam associated with the surface of a liquid as the substance 14, but use with various types of solids and gases susceptible to foaming is also possible.

As background, foam consists of cellular structures in which films or cell walls define outer limits of individual bubbles within the foam. One example of a foam would be soap bubbles on the surface of water. Due to the instability of the foam, the bubbles often "break up" or burst. As the foam "breaks up," it emits transient elastic waves or energy comprising an acoustic emission. Bubble bursting illustrates one example of where acoustic emission occurs and can be monitored by the present invention. The foam also generates acoustic emission when liquid drains within the cell walls of the foam, such as while under the influence of gravity. Additionally, the transport of a gas within a bubble through its cell wall or a pin hole into an adjacent bubble also generates acoustic emission. To characterize the foaming, the sensor 12 may detect or measure all of these modes of acoustic emission and communicate this data to the controller 16, such as via an output signal representative of the acoustic emissions. In the preferred embodiment, the sensor 12 is positioned anywhere in, at or near (collectively "adjacent") the substance 14 susceptible to foaming, and preferably sufficiently close to establish acoustic communication with any foam present. In such position, the sensor 12 may receive passively the acoustic emissions, including within a given frequency range (e.g., 20 Hz to 1 Mhz).

For purposes of this aspect of the invention, a "passive" sensor is distinguished from an "active" one in which an acoustic signal (usually ultrasonic) is both transmitted and received by the sensor (such as for physically detecting the position or location of some object relative to the sensor). The "passive" sensor 12 used in this aspect of the invention may include, but is not limited to, one or more of the following: (1) a contact sensor mounted onto a vessel, container, support, pipe or other solid structure; (2) a hydrophone immersed within a liquid, gas-liquid mixture, gas-bubble mixture, solid-liquid mixture, or solid; or (3) a microphone.

Turning back to the physical properties of foam, the root mean square level of acoustic emission from collapsing bubbles correlates to the amount of energy radiated during the collapse. Generally, high emission intensity relates to high bubble breakup activity and low emission intensity relates to low bubble breakup activity or high foam stability. The sensor 12 detects or "hears" these types of acoustic emissions and allows their characteristics, including intensity and number (hits), associated waveforms and frequencies, amplitude, total energy, rise time, pressure level, etc., to be assessed. This can be accomplished using a controller 16 that receives signals representative of the acoustic emissions, which may be a corresponding electrical output signal (e.g., voltage) received from the sensor 12. A signal processor and/or amplifier may be associated with the controller 16 for increasing the strength of the signal received (not shown) and a computer system 16a operational for recording, processing, interpreting, or displaying the emission data received.

The controller 16 and, in particular, the computer system 16a forming part of it, may be programmed to identify desired characteristics for the particular acoustic emissions of a given process or object. For instance, during a certain process, a user may wish to only monitor the intensity of the acoustic emission(s). Therefore, the controller 16 may be programmed only to monitor this single characteristic using the output signal provided. Additionally, the controller 16 may monitor several characteristics and analyze the resulting data with respect to changes over time.

Besides monitoring and/or recording this information, the instrument 10 may be used as part of a system to automatically control the foaming. For example, a predetermined or known threshold value representing an acceptable level of foaming for the particular object or process being monitored may be provided to the controller 16. The threshold value may be the achievement or loss of a certain intensity level, number of hits, and/or frequency spectral characteristics, at any particular time or over a given period. The user may determine this threshold value from previous experience yielding empirical data, mathematical calculations, or otherwise. Preferably, the threshold value is set such that the foaming may be controlled before reaching a predetermined desirable or undesirable level.

The controller 16 may be programmed to produce an output signal for actuating a feedback response upon receiving acoustic emission data values approaching or exceeding the predetermined threshold value. This response may include any type of user-identifiable output, such as sounding an alarm, illuminating a light, or displaying data (which may include details of the acoustic emissions) on a display device (such as by sending an e-mail message, updating a web site, etc.). Additionally or alternatively, the response may involve triggering an actuator 16b associated with the controller 16 for automatically taking measures to control the foaming (such as by adding an anti-foaming agent or foam suppressant, reducing the liquid level, halting the corresponding process causing or creating the foaming, or otherwise).

To facilitate automated process control, the controller 16 may also communicate with one or more input or output devices 18a, 18b associated with the container or vessel holding the substance 14 susceptible to foaming. An exemplary output device 18a includes a drain. One example of an input device 18b includes a fluid (liquid or gas) connection, such as for introducing sparging bubbles into the fluid, the substance 14 itself, or cleaning fluids (such as water). Another possibility is for the input device 18b to comprise an agitator, such as a mechanical shaker or stirrer.

In addition to using a single passive sensor 12 to monitor foaming via acoustic emissions, it is also possible to make simultaneous or concurrent use of multiple sensors to determine the relative location of foaming activity. For example, multiple sensors can be placed adjacent to an object, such as a volume of liquid, susceptible to foaming. Differences in the output signals may then be used or compared to determine the location of foaming "hotspots," which may correspond to a non-uniform consistency or concentration of reactants and products. Appropriate adjustments or corrective measures can then be taken.

Reference is now made to the following practical examples, which are in some instances prophetic. Moreover, although described with particularity, these examples should not be viewed as limiting the scope of the invention.

EXAMPLE 1

Cement/Concrete Foam Index

With reference to the schematic illustration of FIG. 1, this example is provided to illustrate how the instrument 10 might be used to automate a known process for determining the foam index of mineral admixtures used in and of concrete. As background, a typical procedure for visually testing a mineral admixture may involve the following steps: (1) combining a standard, diluted AEA with distilled water (1AEA:20H$_2$O); (2) placing 20 g of cement or pozzolan in a 4 fluid ounce bottle, add 50 ml of distilled water to bottle, cap and shake for 1 minute to thoroughly wet the cement; (3) adding the diluted AEA in 0.2 ml aliquots, with vigorous shaking for 15 seconds after each aliquot; (4) laying the bottle on its side and observing foam stability; and (5) determining the foam index by visually assessing the amount of dilute AEA, in ml, needed to produce a stable foam; i.e., one in which no bubbles can be seen breaking for a period of 15 seconds. As can be appreciated, this visual process is highly subjective.

Using the instrument 10, the test process is made objective and can thus be automated. For example, using the set-up shown in FIG. 1, a baseline amount of an additive, such as an air entraining agent—for example, the sodium salt of dodecylbenzenesulfonic acid ($C_{12}H_{25}C_6H_4SO_4Na$)—may be combined with a test sample forming the foaming substance 14, which may already include water. A sensor 12 associated with this substance 14 communicates with the controller 16 to relay output signals indicative of acoustic emission(s) as the AEA is added. In this instance, the controller 16 receives the number of hits (i.e., the energy pulses detected by the acoustic sensor 12, such as may be created as bubbles burst) over a period of time, and may display this information on a suitable device, such as a monitor.

By recording the change in the number of hits as the total amount of AEA increases, the user can determine if the optimal amount of AEA has been added. The AEA may be automatically added by the test instrument 10 from a source 20, such as a titrator, controlled or activated by the actuator 16b, or instead may be manually added. Moreover, an agitator such as a mechanical shaker or stirrer forming an input device 18b may receive output signals from the controller 16 to agitate the substance 18 and thus admix the newly added AEA.

In addition to recording the number of hits, the controller 16 may record the sound pressure level and the acoustic frequency. Monitoring or analyzing specific frequency ranges and detecting intensity versus time or other process variables assists in defining the interaction of AEA with the mix. This in turn allows for a determination to be made regarding the amount of AEA to be added for establishing the correct amount of entrained air specified or called for by code, regulation and/or condition to which the concrete is exposed.

Figure 1A:
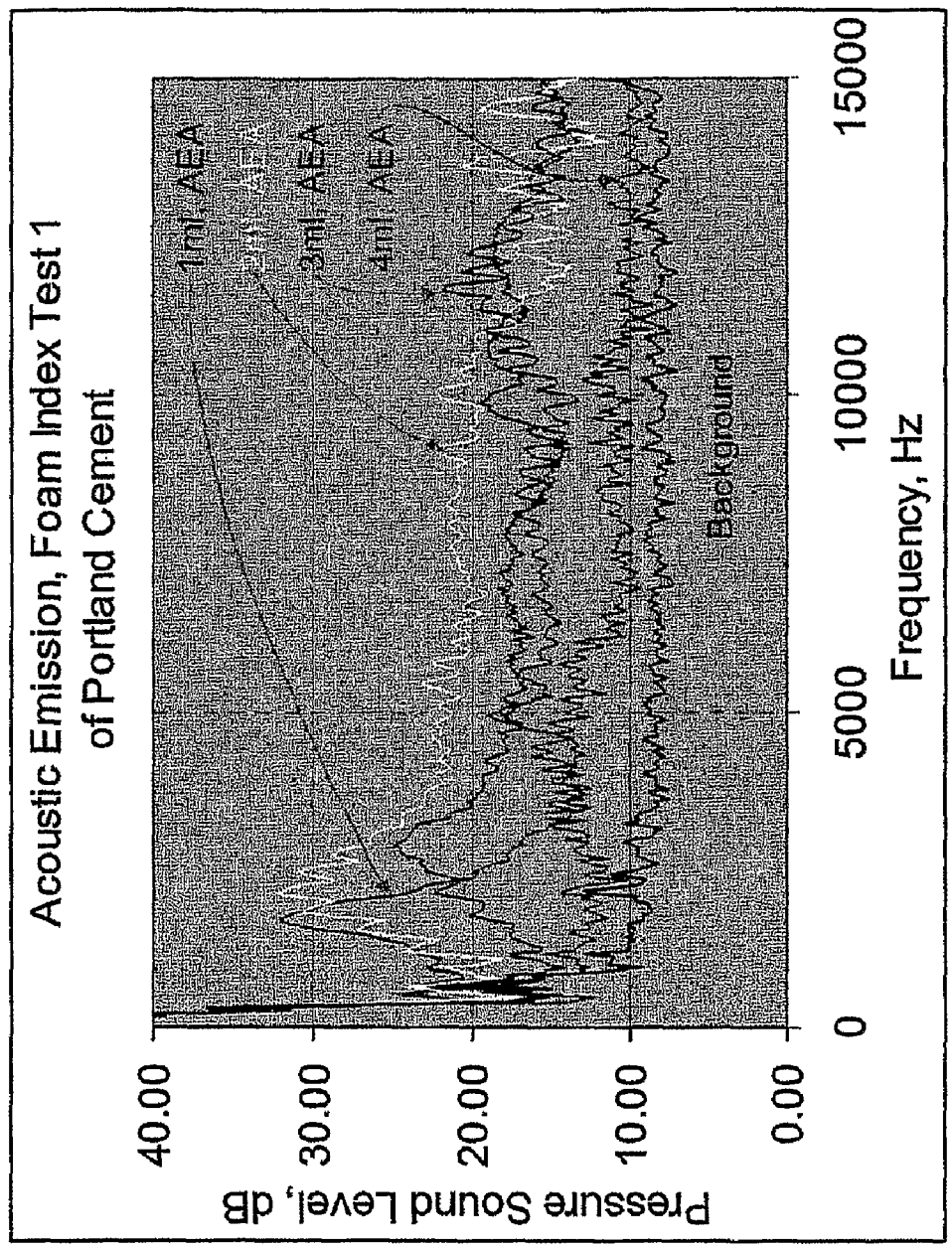
Figure 1B:
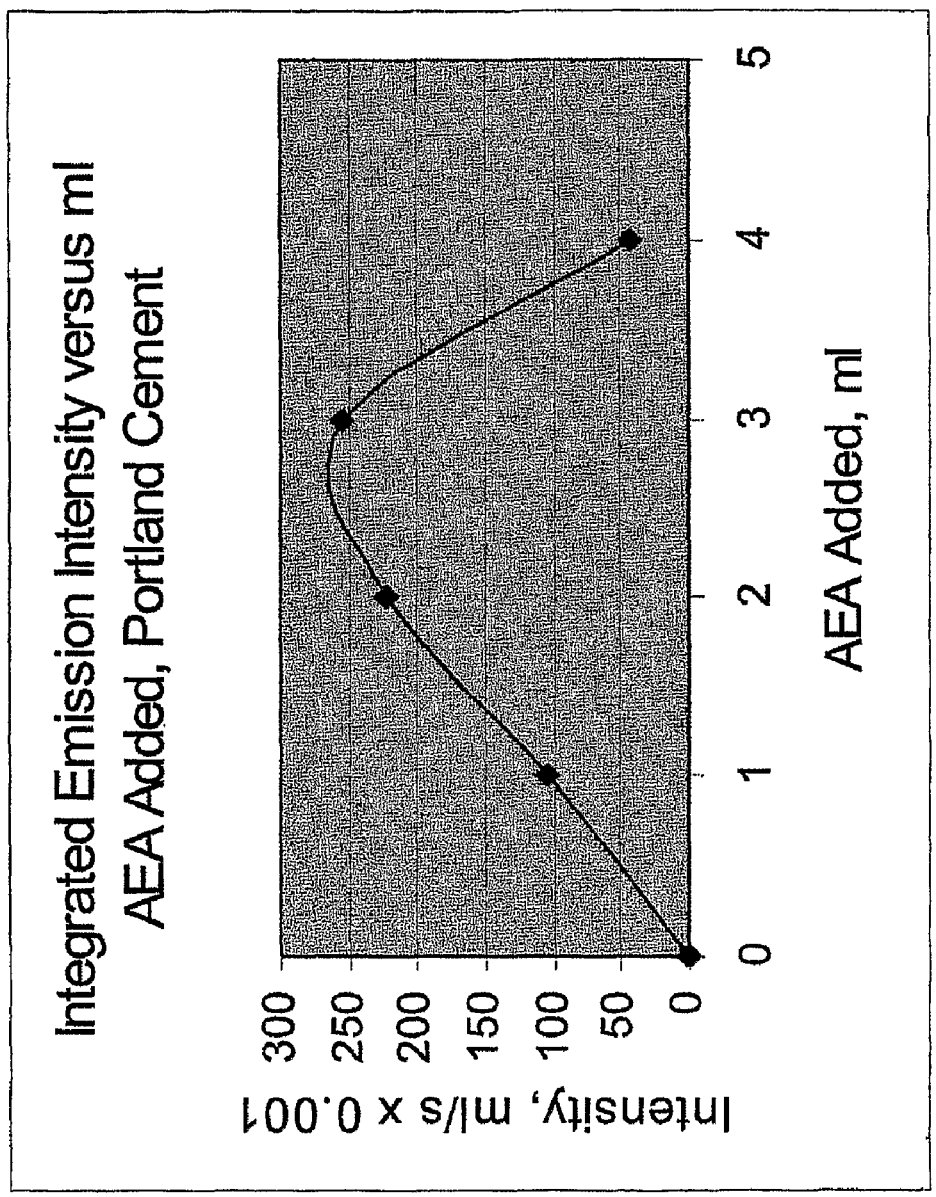

FIG. 1a illustrates one experiment conducted using Portland Cement. After AEA addition, the spectra show that foam break-up produces both narrow bands and a broadly-distributed signal. In particular, after adding 1 ml of an AEA, a narrow emission band was observed at 1,750 Hz; it broadened and moved to 2,150 Hz upon adding 2 ml of an AEA, and again broadened and moved to 2,950 Hz upon adding 3 ml of an AEA. After 4 ml AEA, no narrow bands were observed and the background emission level was very low. An average, integrated signal intensity over the 0-to-15 kHz frequency range is plotted in FIG. 1b. The intensity increased rapidly as the amount of the AEA was increased up to 3 ml; between 3-to-4 ml of the AEA, the intensity dropped by over 80%.

These data show that the intensity of the acoustic emissions increased with the increased addition of the AEA, and then decreased dramatically when stable bubbles were created. First, with a very weak foam, the primary sound intensity comes from the breaking of very few bubbles or background noise (i.e., low-to-moderate intensities); second, as the amount of foam increases but is still unstable, the sound intensity increases dramatically from a plethora of unstable bubbles; third, the foam stabilizes at which point the emitted sound decreases dramatically.

By comparison, the conventional visual foam index procedure gave an average value of 3.5 ml. A value between 3-to-4 ml (FIG. 1b) was also obtained from the acoustic emission results. Therefore, these data provide credence to using acoustic emissions as a way to automatically measure the foam index. Furthermore, they suggest that foam or emulsion stabilities in other materials or applications should also be measurable using the arrangement shown in FIG. 1.

As a subset of this example, manufacturers are required to certify the age of AEA's supplied to users according to a specification (currently ASTM C 260 Standard Specification). As background, liquid AEA's may have a limited shelf life, after which their foaming characteristics degrade. Therefore, AEA manufacturers continually check their stock and look for inexpensive, alternative chemistries that have acceptable foaming properties and long shelf life. It is appreciated that such qualification testing of AEA formulations is common practice and performed by manufacturers to compare and quantify foaming and air entraining properties relative to an expensive and industrially-accepted standard, obtained from wood-vinsol resin (NVR).

One of these tests involves placing an AEA/water mixture in a glass container, stirring or shaking it vigorously, measuring the height of the foam layer created above the water layer, and then measuring the height of the foam one hour-to-four hours later. The acoustic emission emanating from the foam layer during this test may be monitored to continuously define foam stability. The automated foam index test instrument 10 disclosed herein may thus provide quantitative foam stability information and important AEA stability information.

EXAMPLE 2

Wastewater Treatment Plant

In another embodiment, the instrument 10 is used for monitoring and/or controlling foam associated with wastewater treatment, such as for example, in aeration tanks at municipal and industrial plants. As shown in FIG. 2, the sensor 12 and a source 20 of foam suppressant may be positioned adjacent a tank 22 for receiving the wastewater or other foaming liquid qualifying as the substance 14. In the preferred embodiment, the tank 22 includes an aerator and a controller 16 positioned at a remote location. For instance, the controller 16 may be located in a separate building at the wastewater treatment site or even remote from the treatment site.

In use, the instrument 10 then "listens" to the foam to provide remote monitoring. For example, the sensor 12 may receive the acoustic emissions generated by the foam, including possibly intensities, waveforms, amplitudes, energy, rise time, and frequency of these emissions. In the automated set up, an operator (such as an engineer or technician) inputs the desired emission characteristic for the controller 16 to monitor. For instance, the operator may instruct the controller 16 to record the emission intensity over a period of time. From previous experimentation or mathematical calculation, the operator may set a threshold value representing an excessive foaming condition. At this point, the operator is free to leave the control area since the test instrument 10 will automatically control the foam level. The sensor 12 receives/detects the emissions data and communicates the data to the controller 16.

Besides remote monitoring, the test instrument 10 may automatically provide the feedback response necessary to control the wastewater foam without the need for constant monitoring by a human. For example, if the controller 16 receives a value approaching or in excess of the preset threshold value, it may cause a feedback response (such as sounding a visual or audible alarm, dialing a telephone number, sending an e-mail message, updating a web site, etc.) or automatically initiate defoaming activity (such as by adding a foam suppressant). Therefore, the foaming may be controlled prior to any deleterious event, such as an overflow, possibly without human intervention.

FIG. 2a graphically illustrates the potential benefit that may be achieved using the instrument 10 over a weekend as a wastewater treatment site, as shown in FIG. 2. As illustrated, excessive foaming on the top of the aeration tank 22 begins around 8 a.m. on Saturday morning, causing the intensity of the acoustic emissions to increase. By around 1 a.m. on Sunday morning, it is severe enough for the instrument via controller 10 to generate an alert signal (labeled as 'Alert Operator'). At some time later, labeled as 'Adjust Operation', the operator or the foam suppressant system including the source 20 of a defoaming agent intervenes to control excessive foaming. With intervention (shown by the line with diamonds in FIG. 2b) the foaming event is managed without system upset or sludge spillage before the 8 a.m. shift arrives on Monday morning ('Event Ends').

In another scenario, assume that the instrument 10 is in place and measures sound intensity but no alert or feedback is employed. In this case, the data of FIG. 2a (in particular, the line with squares labeled 'Unchecked Foaming') shows acoustic intensity measured by the instrument 10 as foaming and foam height increases in the aeration tank. As can be seen, the acoustic emission increases, and then decreases as the foam thickness becomes excessive because of foam stability (i.e., stable foams mean stable bubbles and less acoustic emission is detected). As workers arrive around 8 a.m., excessive foaming is observed and measures are taken to manually adjust operation. This may lead to foam instability, increased sound emission as more bubbles start to break, and finally control of the excessive foaming approximately thirty hours later than in the case of the instrument 10 alerting the operator. During this thirty hours, a system upset and sludge spillage could have occurred, which could necessitate a large scale clean up operation at great expense.

EXAMPLE 3

Foam Curing/Production

In another embodiment, the automated foam index test instrument 10 may be used to monitor and control the heating/curing of foams. In one example, as shown in FIG. 3, polyimide foam is created by placing a "balloon" precursor material and foaming agent (together forming the substance 14) in a heat input source 20 or "heater," such as a furnace. The temperature is then increased and held at a certain level or range of levels for a given period of time.

During heating, the "balloon" precursor material expands and, with the aid of the foaming agent, creates a polyimide foam consisting of open and closed microspheres. The expansion of the "balloon" may cause bubble breakage, transport of gas between bubbles, and liquid drainage between bubbles. By monitoring the acoustic emissions during this sequence using an associated sensor 12, the instrument 10 may provide real-time monitoring of the foam being formed and provide any necessary feedback control (such as by adjusting the temperature of the "source" 20, or furnace) to ensure that the desired end product results.

EXAMPLE 4

Foam Flotation/Fractionation

In another embodiment, shown in FIG. 4a, the instrument 10 may be used to provide real time feedback or automated control of a system including a liquid column 24, or any other similar process (referred to as "foam flotation" or "fractionation"). Such systems take advantage of the surface activity of constituents (e.g., their hydrophobic or hyrophilic nature), and typically involve bubbling a gas such as air, nitrogen, or carbon dioxide through a solution, in which the surface active constituents adsorb to the gas-liquid interface of the bubbles. The bubbles rise to the top of the liquid pool/column and form a product-rich foam layer. In this foam layer, liquid drains from between the bubbles back into the liquid pool, further concentrating the foam layer. Finally, foam becomes collected and collapsed, resulting in a product-rich solution.

The instrument 10 as disclosed may be used to characterize the acoustic emission generated from the bubbles in the liquid layer and from the foam adjacent the top of the corresponding liquid column 24 (which is associated with a reservoir 26 for recovering the concentrated product). The instrument 10 may include at least one and possibly more sensors. For example, as shown in FIG. 4a, three such sensors, 12a, 12b, 12c may be positioned at the liquid layer, the lower portion of the foam layer, and at the top of the foam layer, respectively. In the illustrated embodiment, the sensor 12c positioned at the liquid layer is a hydrophone and may thus be at least partially submerged. An outlet O may also be provided for extracting residue from the column 24.

By measuring one or more of the sound pressure, frequency response and spectrum, number of hits, and rise times, the bubble movement, oscillation, and bursts may be characterized. Additionally, the sensor 12 may measure the drainage of the interstitial liquid between bubbles, bubble size/coalescence, and inter-bubble gas diffusion. Through monitoring of one or more of these variables, the controller 16 may regulate the liquid $I_1$, gas $I_2$, and reactant $I_3$ inputs to the column 24 to increase the product extraction efficiency.

FIG. 4b shows acoustic emission data from a liquid feed solution during foam fractionation of a model protein, bovine serum albumin (BSA). It is known that flow rates between 0-4 ml/min produce high BSA enrichments but low fractionation recoveries; flow rates between 8-10 ml/min provide high enrichments and recoveries, and flow rates above 10 ml/min give low enrichments and high recoveries. As can be seen from FIG. 4b, the acoustic emission also has three distinct patterns $P_1$, $P_2$, $P_3$ for the flow rates of 0-4 ml/min, 6-10 ml/min, and >10 ml/min. This emission data illustrate a distinct difference as the gas flow rate in a 5 cm diameter column increased from 4 to 12 ml/min, as three emission bands were detected at 1,250 Hz, 1,050 Hz and 600 Hz. Hence, distinctive acoustic emissions can indeed be detected using the instrument 10.

EXAMPLE 5

Foam Index Test Comparisons

Experimental testing has confirmed that the foam index (FI) of mineral admixtures used in concrete could be measured using acoustic emission techniques. For the experiments, the instrument 10 included a one-liter glass cell 30, as shown in FIG. 5. This cell 30 included a sealable, AEA dosing port 32 at the top; a ported lid 34 for a microphone 36 (Brüel & Kjær, 4189, ½" prepolarized, free-field) and which, upon removal, enabled sample and water introduction/extraction; a contact sensor 38 (Physical Acoustics, R1.5 with integral amplifier) mounted on the outside of the cell 30; and an additional side port 40 for a hydrophone 42 (Brüel & Kjær, 8106, high sensitivity). The ability to measure acoustic emissions using three different sensors 36, 38, 42 provided comparative analyses. For comparative purposes, testing was completed both in the laboratory setting and in an anechoic chamber.

During use, the cell 30 was held firmly in place, such as by a rubber-coated ring clamp (not shown). An agitator in the form of a stirrer 44 associated with a magnet 46 mounted on top of the shaft of the stir motor 48 capable of rotational speeds of up to 3750 RPM was used to agitate the mixture 14 in the cell 30 and thus assist in creating foam. Examining the performance of the stirrer 44 in liquids and liquid-plus-solid mixtures showed that rotational speeds near 1800 RPM created smooth operation and high foaming capacity. The stir motor 48 was turned on-and-off using a manual switch and voltage controller (not shown).

The test procedure performed included the following steps: (1) combining standard, diluted AEA (dodecylbenzenesulfonic acid) with distilled water (1AEA:20H$_2$O); (2) placing 40 g of cement or coal combustion ashes (CCA) into the cell 30, adding 100 ml of distilled water, capping the cell 30, and stirring at about 900 RPM for 1 minute to thoroughly mix the contents; (3) 30 seconds after turning off the stirrer, acquiring background acoustic emission data to establish sensor threshold; (4) adding the diluted AEA in 0.2 ml aliquots (which was done using a digital micropipette to standardize and quantify the amount added) and stirring at 1800 RPM for 15 seconds; (5) turning off stirrer, and then waiting for seven seconds before visually observing foam stability and/or acquiring the acoustic emission data; (6) acquiring acoustic emission data for 15 or 30 seconds, while also observing foam stability; (7) determining the FI of the sample based on the amount of dilute AEA needed to produce a stable foam from visual and acoustic emission signal observations; and (8) comparing the visual and acoustic emission data.

Data acquisition was achieved using a controller 16 including: (1) a Physical Acoustics PCI-2 two channel acoustic emission card and associated AEWin software running on a computer; and (2) a PC-based Noise & Vibration Analysis (NVA) system and a Nexus pre-amplifier for microphone data assessments.

For the PCI-2 system, each waveform was captured when the amplitude was greater than a preset threshold level. For purposes of this experiment, this threshold level was determined by collecting acoustic emission data before dosing AEA into the samples and stirring. In the laboratory setting, these thresholds were: 27±3 dB (microphone) and 29±3 dB (contact sensor). In an anechoic chamber, thresholds were: 26±1 dB (microphone) and 24±2 dB (contact sensor).

Each waveform was then assessed using the software. For the NVA system, the sound pressure level (SPL, in dB) was collected over a 100 Hz-to-20 KHz region for the duration of each foam index test or for sequential, one minute intervals in assessing the foam stabilities of AEA'S. FIG. 6 pictorially represents an acoustic emission waveform and various characteristics of it that may be assessed.

Foam stability (FS) assessments involved adding 200 ml of dissolved 5% AEA:95% H$_2$O to the glass cell 30, foaming the AEA using vigorous stirring for four minutes or until a stable foam height was achieved, and then measuring the acoustic emissions from the cell 30 continuously for periods up to one hour using both microphone and contact sensors 36, 38. Three AEA's were tested, including DBS (dodecylbenzenesulfonic acid), SILIPONRN 6031 (sodium lauryl sulphate, Aqualon Hercules Inc.) and SILIPON RN 8018 (ethoxylated fatty alcohol, Aqualon Hercules Inc.). The tests using the microphone 36 with the NVA system entailed data accumulation and averaging over 100 Hz-to-20 kHz during sequential one minute intervals. The use of the Physical Acoustics system with contact and microphone sensors 36, 38 entailed continuous data accumulation/storage during the entire test for over one hour.

The loss on ignition (LOI) measurements were accomplished by placing 1 g of CCA into a furnace at 750° C. for one hour, and then the weight loss of the CCA was measured. This loss is predominantly caused by the oxidation of unburned carbon in the samples because their moisture contents were typically ≦0.2. Unburned carbon selectively absorbs AEA and prevents its ability to instill air into concrete.

As noted above, visual foam index determinations depend on a person observing bursting bubbles on top of foam layers, whereas foam index determinations made using the instrument 10 depend on monitoring acoustic emission activity both within and on foam layers. Results from the visual foam index procedure were compared to the acoustic emissions acquired from the contact sensor, microphone and hydrophone 36, 38, 42. The characteristics of the acoustic emission waveforms assessed included: number of hits, number of counts, signal amplitude, signal rise time, and signal duration. The number of hits (#Hits) and changes therein during AEA dosing precisely replicated visual foam index observations.

Figure 7:
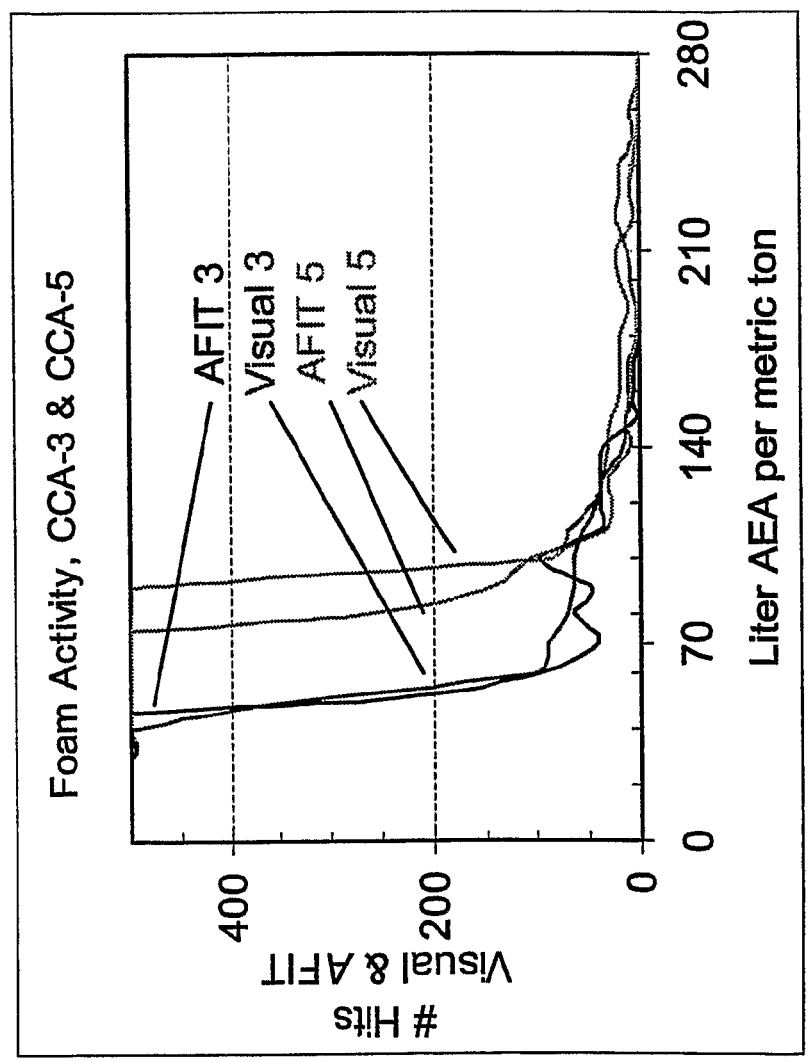

This replication, displayed in FIG. 7 for two CCA samples, included: very high surface bubble breakage and the number of hits at low AEA dosage; this activity was followed by a rapid decline in both visual and the number of hits data; the overall activity then entered a low intensity plateau region at intermediate AEA dosages where the number of bubbles bursting and the number of hits was small (~50); after this plateau, the visual number of bubbles bursting approached zero and the acoustic emissions monitored stabilized at near zero for the remainder (15 or 30 seconds).

Figure 8:
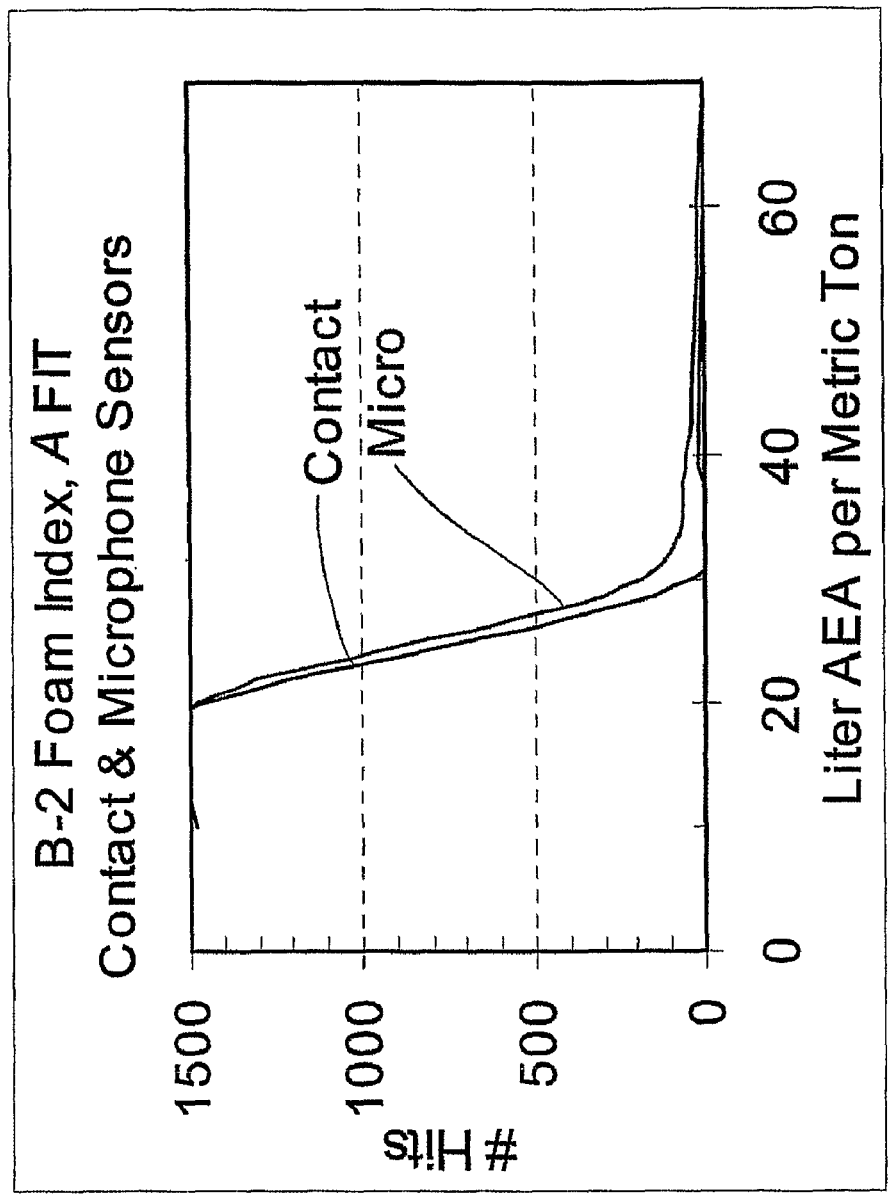
Figure 9:
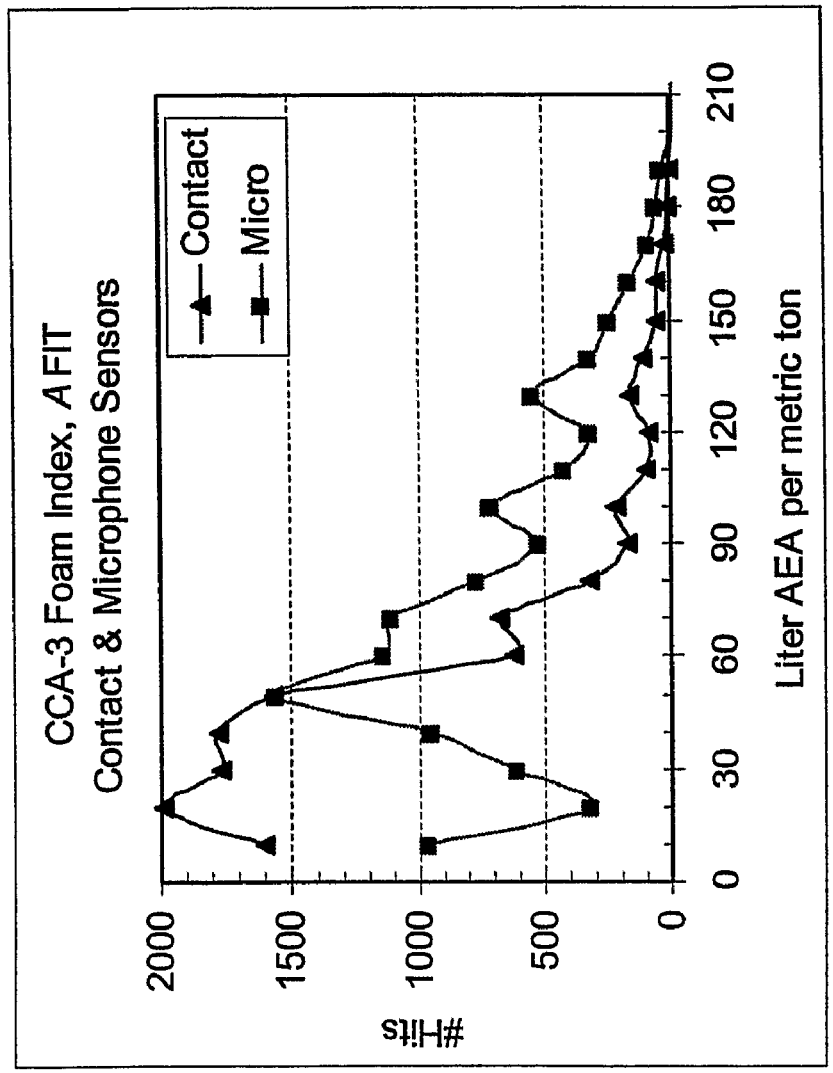

Comparisons between acoustic emission data from microphone 36 and contact 38 sensors are displayed in FIGS. 8 and 9. For sample B-2 in FIG. 8, the number of hits decreased rapidly for both sensors starting at an AEA dosage of 20 l/Mton; then attained the low signal, plateau region between AEA dosages of 30-to-60 l/Mton; and finally approached zero at dosages of 68 l/Mton (contact sensor) and 75 l/Mton (microphone). For sample CCA-3 in FIG. 9, the shape of the curves at AEA dosages $\leq$50 l/Mton are somewhat different, but acoustic emission signal maxima at dosages of 55, 70, 100 and 130 l/Mton are identical for both sensors; the number of hits approached zero at an AEA dosage of 195 l/Mton for both sensors.

Figure 10:
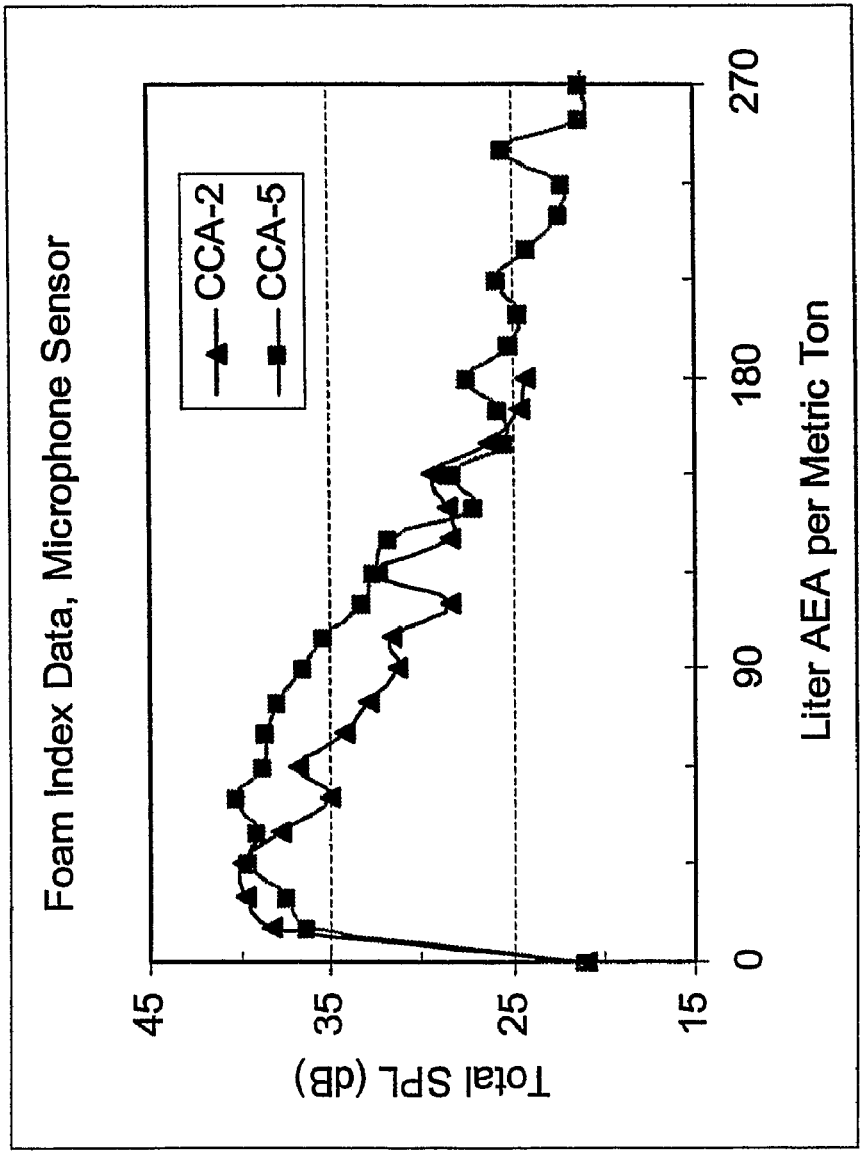

Characteristics of foam index data acquired using and a microphone 36 are presented in FIG. 10. The background SPL was low before AEA addition. It increased rapidly with increasing AEA dosage and, then at an intermediate amount of AEA, the SPL again decreased. The breadth of the high SPL portion grew with increasing foam index values. The SPL at the end of each foam index test never attained the low value it had at the beginning of the test.

Different mathematical functions were used to fit the decreasing portion of the SPL curves so foam index values could be calculated. The most reproducible fits employed a three parameter, simple exponential function having the form: $SPL=ae^{[b/(x+c)]}$, where a, b and c are fitting parameters and x is the AEA dosage. The foam index was calculated as that dosage at which the SPL decreased by $2\sigma$, i.e. 95%, between its maximum and minimum values.

Table 1 compares foam index values, given in drops AEA (200 µl each), from acoustic emission and visual testing. The acoustic emission data are from contact and microphone sensors with 15 second and 30 second collection periods.

TABLE 1

Average foam index values (in drops AEA, each 200 µl) and deviations from acoustic emission and visual measurements.

| | Contact Sensor | | Microphone | | Microphone | Visual |
|---|---|---|---|---|---|---|
| Sample | 15 s, #Hits Ave ± 2σ | 30 s, #Hits Ave ± 2σ | 15 s, #Hits Ave ± 2σ | 30 s, #Hits Ave ± 2σ | 15 s, SPL Ave ± 2σ | 15 s, #Hits Ave ± 2σ |
| ISG-1 | 10.4 ± 1.0 | 10.3 ± 1.2 | 15.4 ± 8.2 | 19.1 | 10.6 ± 4.2 | 12.0 ± 3.6 |
| ISG-2 | 16.6 ± 0.8 | 16.7 ± 0.2 | 14.1 ± 6.8 | 14.1 ± 6.2 | 16.1 ± 1.4 | 16.2 ± 3.2 |
| ISG-3 | 18.4 ± 1.2 | 18.8 ± 1.4 | 19.0 ± 1.0 | 19.5 ± 0.6 | 17.8 ± 2.0 | 19.5 ± 1.8 |
| ISG-5 | 26.9 ± 0.2 | 29.3 ± 1.2 | 25.6 ± 2.2 | 25.8 ± 2.2 | 23.0 ± 8.6 | 29.2 ± 4.1 |
| B-2 | 6.6 ± 0.8 | 6.6 ± 1.4 | 6.8 ± 1.6 | 7.2 ± 0.8 | 22.8 | 6.3 ± 2.0 |
| B-5 | 6.7 | 5.9 | 6.7 | 6.7 | 1.8 | 6.8 ± 1.2 |
| B-R | 27.8 | 29.9 | 29.8 | 29.7 | | 26.0 ± 0.0 |
| B-C | 3.7 | 3.8 | 4.5 | 3.6 | | 8.0 ± 0.0 |
| Cum. Dev. | 5.0% | 6.6% | 24.4% | 14.8% | 24.0% | 12.8% |

The range of foam index values in Table 1 represent those typically encountered in the concrete industry. The cumulative ±2σ deviations listed in the last row were as small as 5% for the contact sensor (15 second data) and as great as 24% for the microphone (SPL data). The deviation of the visual data was greater than two times the deviation of contact sensor acoustic emission data. Overall, the data presented in Table 1 shows the concept based on measuring the acoustic emissions during foam index testing was repeatable and should provide highly precise information to industry.

Figure 11:
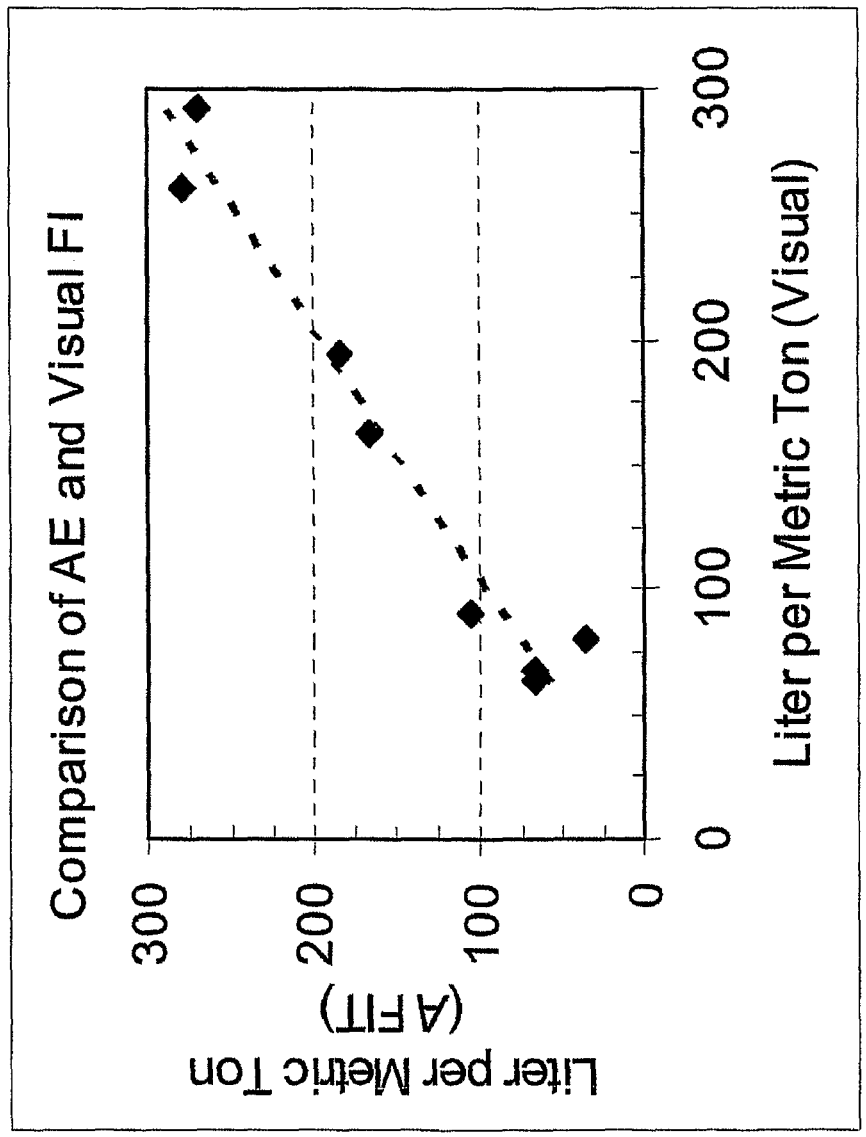

FIG. 11 provides a comparison of acoustic emissions and visual foam index data. The relationship between these visual values is closely represented by a linear equation over abroad AEA dosage range. The linear fit extrapolates through the origin of the plot.

A comparison of acoustic emission data for CCA-3 acquired in the laboratory setting and in an anechoic sound chamber are presented in FIG. 12. Peaks in the number of hits are reproduced in the two data sets, and the difference between the foam index values is less than 8% (178 l/Mton in the lab and 192 l/Mton at the anechoic chamber). Because the laboratory would be as 'noisy' (40-45 dB) as an industrial laboratory, these data confirm the viability of a tabletop instrument 10 for assessing the foam index of CCA's and cement even without sound insulation or vibration isolation surrounding the cell 30. Nevertheless, an instrument designed to control AEA addition to cements and CCA's would be located closer to potentially higher ambient noise levels. Accordingly, some measure of sound or vibration insulation for the instrument 10 may be desirable.

AEA foam stability tests conducted further illustrate the influence of ambient noise. Both contact and microphone sensors were used to listen and characterize foam collapse. However, the higher sensitivity of the microphone provided more insight into AEA foam stability.

The data obtained using a shielded microphone in the anechoic sound chamber after foaming AEA's are presented in FIG. 13. As noted in the legend, the activity rate of DBS was one-hundredth that displayed; whereas the activity rate of 6031 was one-tenth that displayed. Hence, the foam produced by 8018 was very unstable in comparison to the foam produced by DBS or 6031. Peaks in the activity for DBS and 6031 are a result of an 'avalanche and stasis' behavior of bubbles that began to occur at 25+minutes after foaming; highly active bubble collapse for 8018 began ~15 minutes after foaming.

Referring now to another aspect of the invention, a schematic diagram showing the possible design for a tabletop instrument 50 is presented in FIG. 14. The instrument 50 includes an enclosure 52 divided into two sections: one section 52a containing the cell 54 and the other section 52b including pumps (not numbered), reservoirs and the controller 56. Preferably, the cell 54 is a metal vessel having a 250 ml volume and is contained within an insulated or sound-proof chamber 55. A removable lid 58 for the cell 54 provides access for introducing samples, while a removable bottom 60 enables repair of the rotary feedthrough and reuse. Supports 61 associated with the enclosure 52 help to dampen vibrations.

A contact sensor 62 is attached to the outside of the cell 54. In the set-up shown, this type of sensor 62 is preferred, since it will not experience contamination or wear from the solid/water mixtures as would a microphone or hydrophone contained within the cell 30.

In use, an AEA from a source 63 is dosed into the cell at its top through the lid 58 and water is added by a spray nozzle 64 from a reservoir 65. A stirrer 66 is connected to the drive shaft (not numbered) of a motor 70. The control of acoustic emission data acquisition, AEA dosing, water addition before and after a foam index test, the extracting solid/water mixtures after completing a foam index test, and stirring may be accomplished using the controller 56.

The foregoing descriptions of various embodiments of the invention are provided for purposes of illustration, and are not intended to be exhaustive or limiting. Modifications or variations are also possible in light of the above teachings. For example, the instrument 10 may include any number or type of passive acoustic sensors 12 in any arrangement or configuration. Additionally, the controller 16 may include any device capable of receiving, controlling or processing the sensor data. In addition to the examples disclosed, the instrument 10 may be utilized with any process, system, reactor, or otherwise (e.g., by food and consumer product specialists and manufacturers whether emulsifiers and foams provide superior product consistency, shelf life and freshness; by petroleum/oil industries whether new foam formulations provide enhanced oil recovery opportunities; by fire retardant manufacturers whether fire fighting foams meet their requirements under severe and dynamic conditions; and by beverage manufacturers whether the foam is consumer enticing). Additionally, the provisions for controlling the level of foam may include actuating any response. The passive sensor 12 may also form part of a kit including instructions on how to use it in controlling a process with foaming or an object susceptible to foaming. The embodiments described above were chosen to provide the best application to enable one of ordinary skill in the art to utilize the disclosed inventions in various embodiments and with various modifications as are suited to the particular use contemplated. All such modifications and variations are within the scope of the invention.

The invention claimed is:

1. A system for testing a mineral admixture for making concrete associated with the foam, comprising:
    a vessel for receiving the mineral admixture;
    a source of an air entraining agent;
    a passive sensor for generating an output signal representative of an acoustic emission associated with the foam; and
    a controller in communication with the passive sensor for receiving the output signal and providing a response,
    wherein the response comprises a second signal for causing the source to add the air entraining agent to the mineral admixture in the vessel.

2. The system according to claim 1, further including an agitator associated with the vessel, and wherein the response comprises a third signal for activating the agitator.

3. A method of testing a mix used to form concrete, comprising:
    adding a first amount of an agent to the mix;
    detecting one or more acoustic emissions from the mix; and
    determining whether an additional amount of the agent is required based on the detected acoustic emissions.

4. The method according to claim 3, wherein the agent is an air entraining agent and the step of detecting comprises receiving the acoustic emissions from a foam associated with the mix.

5. The method according to claim 3, wherein the adding and detecting steps are accomplished using only a sample of the mix.

6. The method according to claim 5, further including when an appropriate amount of the agent is added to the mix, creating a larger batch of the mix by adding a second amount of the agent proportional to the appropriate amount of the agent added to the sample.

7. A system for testing a mineral admixture for making concrete associated with the foam, comprising:
    a vessel for receiving the mineral admixture;
    a source of an air entraining agent;
    means for passively measuring an acoustic emission from the foam and generating an output signal representative of the acoustic emission; and
    means for receiving the output signal and providing a response,
    wherein the response comprises a second signal for causing the source to add the air entraining agent to the mineral admixture in the vessel.

8. The system of claim 7, wherein the passive measuring means comprises a passive sensor.

9. The system of claim 7, wherein the receiving means comprises a controller.

* * * * *